(12) United States Patent
Madera et al.

(10) Patent No.: US 11,530,128 B2
(45) Date of Patent: Dec. 20, 2022

(54) METHOD AND DEVICE FOR CONTROLLING THE QUANTITY OF LIQUID CONTAINED IN A CARTRIDGE FOR AN AEROSOL GENERATING DEVICE

(71) Applicant: G.D SOCIETA' PER AZIONI, Bologna (IT)

(72) Inventors: Giovanni Madera, Bologna (IT); Gianpiero Lamborghini, Cento (IT); Sergio Morelli, Monterenzio (IT); Eugenio Navacchia, Bologna (IT); Catello Sorrentino, Colorno (IT); Luca Federici, Bologna (IT)

(73) Assignee: G.D SOCIETA' PER AZIONI, Bologna (IT)

( * ) Notice: Subject to any disclaimer, the term of this patent is extended or adjusted under 35 U.S.C. 154(b) by 716 days.

(21) Appl. No.: 16/483,761

(22) PCT Filed: Feb. 20, 2018

(86) PCT No.: PCT/IB2018/051031
§ 371 (c)(1),
(2) Date: Aug. 6, 2019

(87) PCT Pub. No.: WO2018/150394
PCT Pub. Date: Aug. 23, 2018

(65) Prior Publication Data
US 2020/0189903 A1 Jun. 18, 2020

(30) Foreign Application Priority Data
Feb. 20, 2017 (IT) .................. 102017000018745

(51) Int. Cl.
*B67D 7/02* (2010.01)
*A24F 40/70* (2020.01)
(Continued)

(52) U.S. Cl.
CPC .............. *B67D 7/02* (2013.01); *A24F 40/10* (2020.01); *A24F 40/42* (2020.01); *A24F 40/53* (2020.01);
(Continued)

(58) Field of Classification Search
CPC . B67D 7/02; A24F 40/10; A24F 40/42; A24F 40/53; A24F 40/70; B65B 3/28;
(Continued)

(56) References Cited

U.S. PATENT DOCUMENTS 2,999,589 A * 9/1961 Norwich ............... B07C 5/3404
209/523
4,230,195 A * 10/1980 Graffin ...................... B65B 3/28
177/1
(Continued)

FOREIGN PATENT DOCUMENTS

EP 1898189 A2 3/2008
EP 2760768 B1 7/2018
(Continued)

OTHER PUBLICATIONS

International Application No. PCT/IB2018/051031, International Search Report and Written Opinion, dated Feb. 27, 2019.
(Continued)

*Primary Examiner* — Nicolas A Arnett
(74) *Attorney, Agent, or Firm* — Marshall, Gerstein & Borun LLP (57) ABSTRACT

Method and device for controlling the quantity of liquid contained in a cartridge for an aerosol generating device, wherein the cartridge has a container and a liquid contained in the container and wherein, according to which is measured the quantity of liquid contained in the cartridge; and compared the quantity of liquid with a reference quantity of liquid.

6 Claims, 11 Drawing Sheets

(51) Int. Cl.
*A24F 40/53* (2020.01)
*A24F 40/10* (2020.01)
*A24F 40/42* (2020.01)
*G01F 23/20* (2006.01)
*G01F 23/263* (2022.01)
*B65B 31/00* (2006.01)
*F17C 5/00* (2006.01)
*B65B 3/28* (2006.01)

(52) U.S. Cl.
CPC ............... *A24F 40/70* (2020.01); *B65B 3/28* (2013.01); *B65B 31/003* (2013.01); *F17C 5/002* (2013.01); *G01F 23/20* (2013.01); *G01F 23/268* (2013.01); *A61M 2209/045* (2013.01)

(58) Field of Classification Search
CPC ........ B65B 31/003; F17C 5/002; G01F 23/20; G01F 23/268; A61M 2209/045
See application file for complete search history.

(56) References Cited

U.S. PATENT DOCUMENTS

| | | | | |
|---|---|---|---|---|
| 6,800,818 B2* | 10/2004 | Balboni | ............... | B67C 3/202 177/52 |
| 8,266,874 B2* | 9/2012 | Runft | ............... | A61J 3/074 53/900 |
| 8,455,773 B2* | 6/2013 | Trebbi | ............... | G01G 17/00 141/83 |
| 10,167,098 B2* | 1/2019 | Williamson | ............... | G01G 11/00 |
| 10,512,282 B2* | 12/2019 | Bowen | ............... | A24B 15/167 |
| 10,850,874 B2* | 12/2020 | Boldrini | ............... | B65B 3/28 |
| 11,326,930 B2* | 5/2022 | Lanzarini | ............... | G01G 17/00 |
| 11,376,196 B2* | 7/2022 | Ribani | ............... | A61J 3/074 |
| 2007/0062164 A1* | 3/2007 | Gamberini | ............... | B65G 47/843 53/900 |
| 2008/0053211 A1* | 3/2008 | Gamberini | ............... | G01G 17/00 73/149 |
| 2010/0200306 A1 | 8/2010 | Trebbi et al. | | |
| 2011/0126940 A1* | 6/2011 | Herrmann | ............... | G01G 17/00 177/52 |
| 2016/0144458 A1* | 5/2016 | Boldrini | ............... | B23K 31/02 228/176 |

FOREIGN PATENT DOCUMENTS

| | | |
|---|---|---|
| JP | 2007-076921 A | 3/2007 |
| JP | 2007-322422 A | 12/2007 |
| JP | 2008-062994 A | 3/2008 |
| JP | 2014-532014 A | 12/2014 |
| JP | 2016-104008 A | 6/2016 |
| WO | WO-2015/140768 A2 | 9/2015 |
| WO | WO-2016/101202 A1 | 6/2016 |
| WO | WO-2016/177964 A1 | 11/2016 |

OTHER PUBLICATIONS

Office Action, Japanese Patent Application No. 2019-545356, dated Dec. 21, 2021.

* cited by examiner

METHOD AND DEVICE FOR CONTROLLING THE QUANTITY OF LIQUID CONTAINED IN A CARTRIDGE FOR AN AEROSOL GENERATING DEVICE

CROSS-REFERENCE TO RELATED APPLICATIONS

This is the U.S. national phase of International Application No. PCT/IB2018/051031, filed Feb. 20, 2108, which claims the benefit of Italian Patent Application No. 102017000018745, filed Feb. 20, 2017.

TECHNICAL FIELD

The present invention falls within the technical field relating to aerosol generating devices. In particular, the present invention relates to a method and a device for controlling the quantity of liquid contained in a cartridge for an aerosol generating device.

PRIOR ART

Aerosol generating devices are known which comprise a battery, an atomizer which is supplied by the battery and a cartridge containing a liquid. During use, the atomizer heats the liquid contained in the cartridge and the smoker inhales the steam that is produced.

The cartridge consists of a cylinder-shaped container that is filled with liquid and then closed with a cap.

In order to ensure a good quality of smoke, the cartridge must contain a correct quantity of liquid.

In this regard, after the injection of liquid into the cartridge, an operator checks whether the level of liquid in the cartridge exceeds a minimum height.

However, said level check is not very precise and depends on the operator performing the same. Furthermore, this type of control requires the cartridge container to be transparent.

The patent application WO2015140768A2 describes a packaging machine for the production of cartridges for electronic cigarettes and comprising: a filling conveyor which feeds the bottom shells of the cartridges along a filling path; a filling device that is arranged along the filling path to feed from the top a dose of liquid substance inside each bottom shell; an assembly conveyor that feeds the bottom shells along an assembly path; a transfer station in which the bottom shells are moved from the filling conveyor to the assembly conveyor; and at least one assembly device which is arranged along the assembly path to couple a corresponding top cap to each bottom shell. At the end of the filling path (i.e. upstream and downstream of the area in which the bottom shells are filled with the liquid substance), two twin weighing devices are arranged, each adapted to weigh each bottom shell; by weighing each bottom shell before and after filling the bottom shell with the liquid substance, it is possible to accurately measure the quantity of liquid substance that has actually been dosed inside the bottom shell and therefore it is possible to check whether the bottom shell has been correctly filled.

DESCRIPTION OF THE INVENTION

The object of the invention is to provide a method and a device for controlling the quantity of liquid contained in a cartridge for an aerosol generating device which overcomes the aforesaid drawbacks.

The above purpose has been achieved by a method and a device according to the appended claims.

BRIEF DESCRIPTION OF THE DRAWINGS

The present invention will now be described with reference to the attached drawings, which illustrate some non-limiting examples of embodiment thereof, wherein.

PREFERRED EMBODIMENTS OF THE INVENTION

With reference to the attached FIGS. 1-13, a cartridge for an aerosol generating device has been generically denoted with the numerical reference 1.

The cartridge 1 comprises a container 10 and a liquid 11 contained in the container 10.

The container 10 can be made, for example, of stainless steel, plastic or glass.

Preferably, the container 10 has a tubular shape with a circular and constant cross-section along the entire development of the container 10 and has a longitudinal development along a respective development axis X.

The container 10 can comprise a bottom 10a and a side wall 10b which rises from the bottom 10a and which provides a free edge, opposite to the bottom 10a, delimiting an opening 10c of the container 10.

According to a particular embodiment of the cartridge 1, the cartridge 1 comprises an absorbent element 12 (for example made of cotton) arranged in the container 10 which holds the liquid 11 and which has a tubular shape defining a cavity 13.

In particular, also the absorbent element 12 can have a tubular shape having a longitudinal development and can have the cross section having the same shape with respect to the cross section of the container 10. The absorbent element 11 comprises an upper face 11a which faces the opening 10d of the container 10.

Likewise, the cavity 13 can also have a tubular shape having a longitudinal development. In particular, the cavity 13 and the absorbent element 12 are coaxial.

It is understood that other embodiments of the cartridge 1 are allowed without departing from the scope of protection of the present invention. For example, the container 10 could have a square or hexagonal and/or non-constant cross section along the entire development of the container 10.

The method for controlling the quantity of liquid 11 contained in a cartridge 1 for an aerosol generating device is described in the following.

The method comprises the steps of measuring the quantity of liquid 11 contained in the cartridge 1 and comparing the quantity of liquid 11 with a reference quantity of liquid.

The proposed method involves performing a measurement of the quantity of liquid 11 contained in the cartridge 1 (for example, by measuring the weight of the liquid 11 and/or the electrical capacity of the liquid 11).

Advantageously, the control of the quantity of liquid 11 is precise, independent of the operator and does not necessarily require the container 10 to be made of transparent material.

In the event that the quantity of liquid 11 differs from the reference quantity of liquid, the method can comprise the step of discarding the cartridge 1. In particular, the method comprises the step of discarding the cartridge 1 in the case where the quantity of liquid 11 differs from the reference quantity of liquid above a given threshold value.

In order to determine the reference quantity of liquid, a reference cartridge is used which comprises a container equal to the container 10 of the cartridge 1 (same shape, size and material). Moreover, the reference cartridge has a known quantity of liquid inside the container: this means that, for example, the weight of the reference liquid and/or the electric capacity of the reference liquid is known).

According to a first embodiment of the method object of the present invention, the quantity of liquid 11 in the container 10 is determined by measuring the weight of the liquid 11. Accordingly, the reference quantity of liquid is identified in the weight of the reference liquid contained in the reference cartridge.

In detail, the step of measuring the quantity of liquid 11 comprises in the order of the following steps: weighing the container 10 (without liquid 11 inside) of the cartridge 1; injecting a quantity of liquid 11 into the container 10; weighing the cartridge 1 (that is, the container 10 with liquid 11); calculating the weight of the liquid 11 contained in the container 10.

The weight of the liquid 11 is determined by subtracting the weight of the container 10 from the weight of the cartridge 1.

Advantageously, this method allows to have a precise measurement in a simple manner.

According to a second embodiment of the method object of the present invention, the quantity of liquid 11 in the container 10 is determined by measuring the electrical capacity of the liquid 11. Accordingly, the reference quantity of liquid is identified in the electrical capacity of the reference liquid contained in the reference cartridge.

In this case, the step of detecting the quantity of liquid 11 comprises the following steps:
- arranging the liquid 11 contained in the cartridge 1 between a first conductor element 5 and a second conductor element 6;
- electrically charging the first conductor element 5 and the second conductor element 6 with opposite charges;
- calculating the electrical capacity and/or the dissipation factor between the two conductor elements 5 and 6.

The electrical capacity and/or the dissipation factor are indicative of the quantity of liquid 11 contained in the container 10. Advantageously, the measurement of the electrical capacity and/or of the dissipation factor is independent from the dimensions of the container 10 of the cartridge 1.

Figure 10:
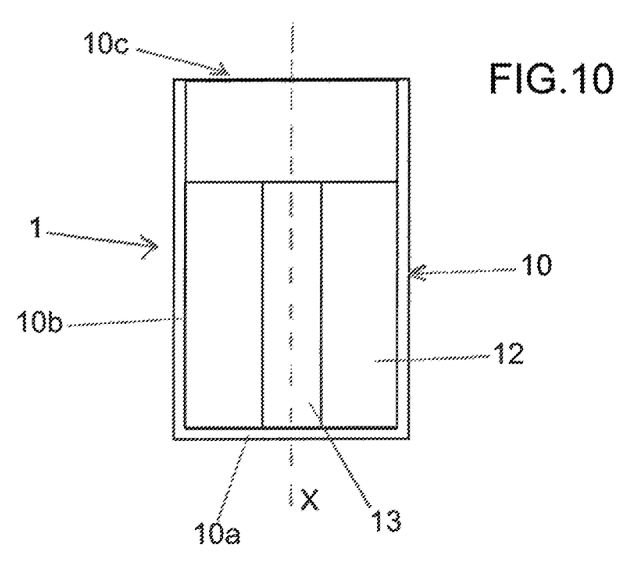
FIGS. 10 and 11 are schematic views respectively in cross-section and from above of a cartridge.
Figure 11:
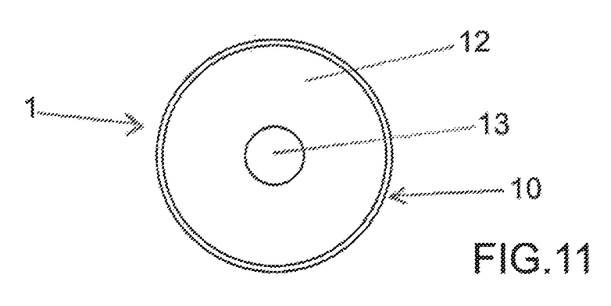
Figure 12:
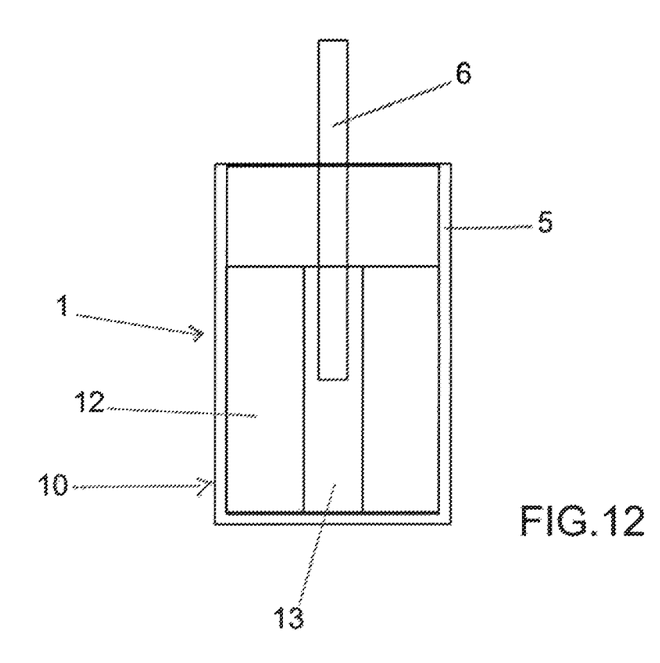
FIGS. 12 and 13 are schematic cross-sectional views of operative steps of different embodiments of the method object of the present invention.

With reference to FIGS. 10-12, the container 10 of the cartridge 1 is made of a conductor material (for example, steel) and the cartridge 1 comprises an absorbent element 12 arranged in the container 10 which holds the liquid 11 and which has a tubular shape defining a cavity 13. In this case, the container 10 is identified in the first conductor element 5 and the method comprises the step of inserting the second conductor element 6 into the cavity 13 of the absorbent element 12 before calculating the electrical capacity and/or the dissipation factor.

Figure 13:
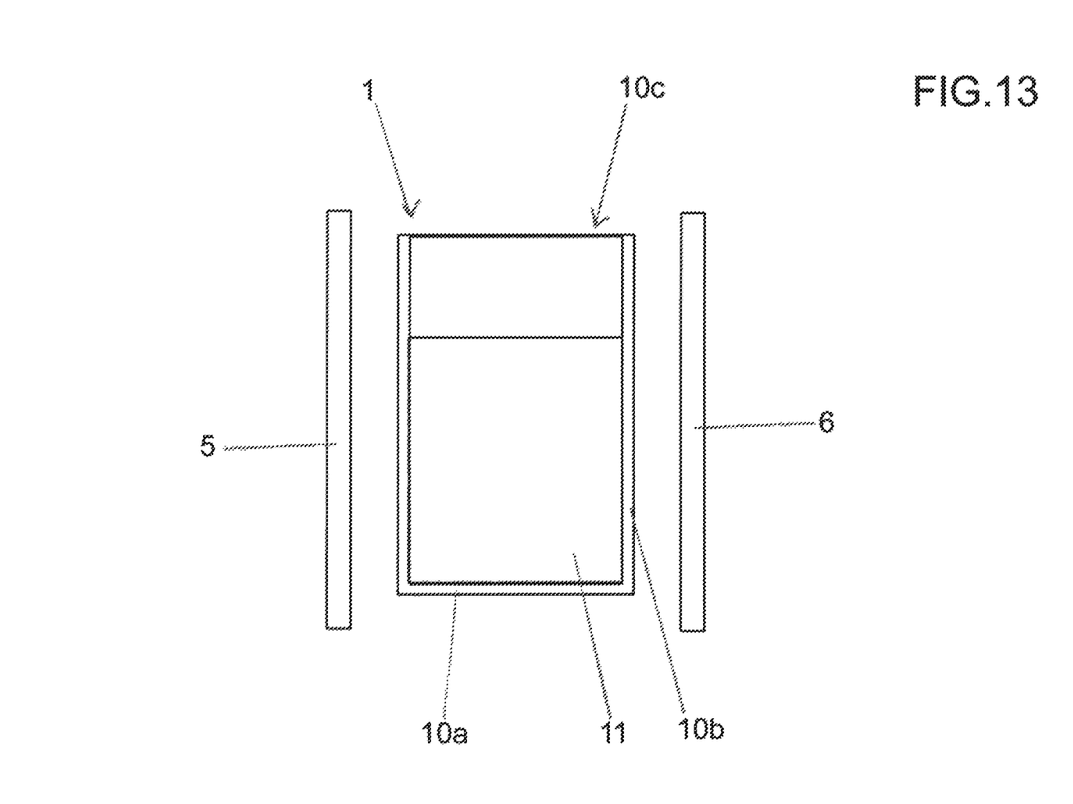

In the case in which the container 10 of the cartridge 1 is not made of a conductor material (for example, of plastic material), the first conductor element 5 and the second conductor element can be two plates (FIG. 13).

The device 7 for controlling the quantity of liquid contained in a cartridge 1 for an aerosol generating device is described in the following.

The device 7 comprises: measuring means 8 for measuring the quantity of liquid contained in the cartridge 1; a processing unit (not illustrated) connected to the measuring means 8 for receiving the data measured by the measuring means 8 and comparing it with a reference quantity of liquid.

According to FIGS. 1-9, a first embodiment of the device 7 is described in the following. In particular, this first embodiment of the device 7 allows to determine the weight of the liquid 11 contained in the container 10.

In said embodiment, the measuring means 8 comprise a first weighing group 80 for weighing at least one container 10 of a cartridge 1 before being filled with the liquid 11 and a second weighing group 81 for weighing the container 10 containing liquid 11.

Figure 1:
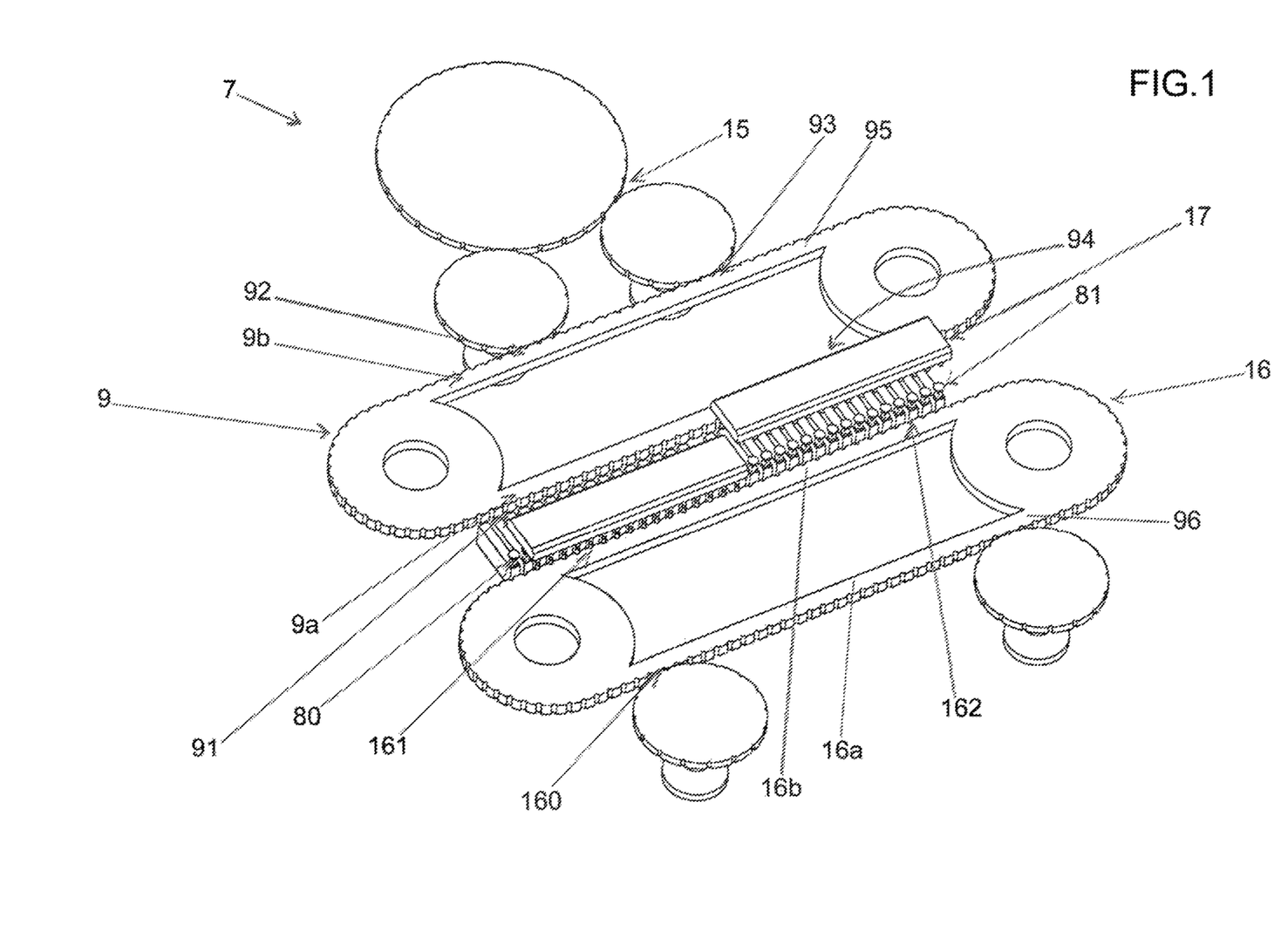
FIGS. 1 to 9 are views of an embodiment of the device object of the present invention in respective operating steps.
Figure 2:
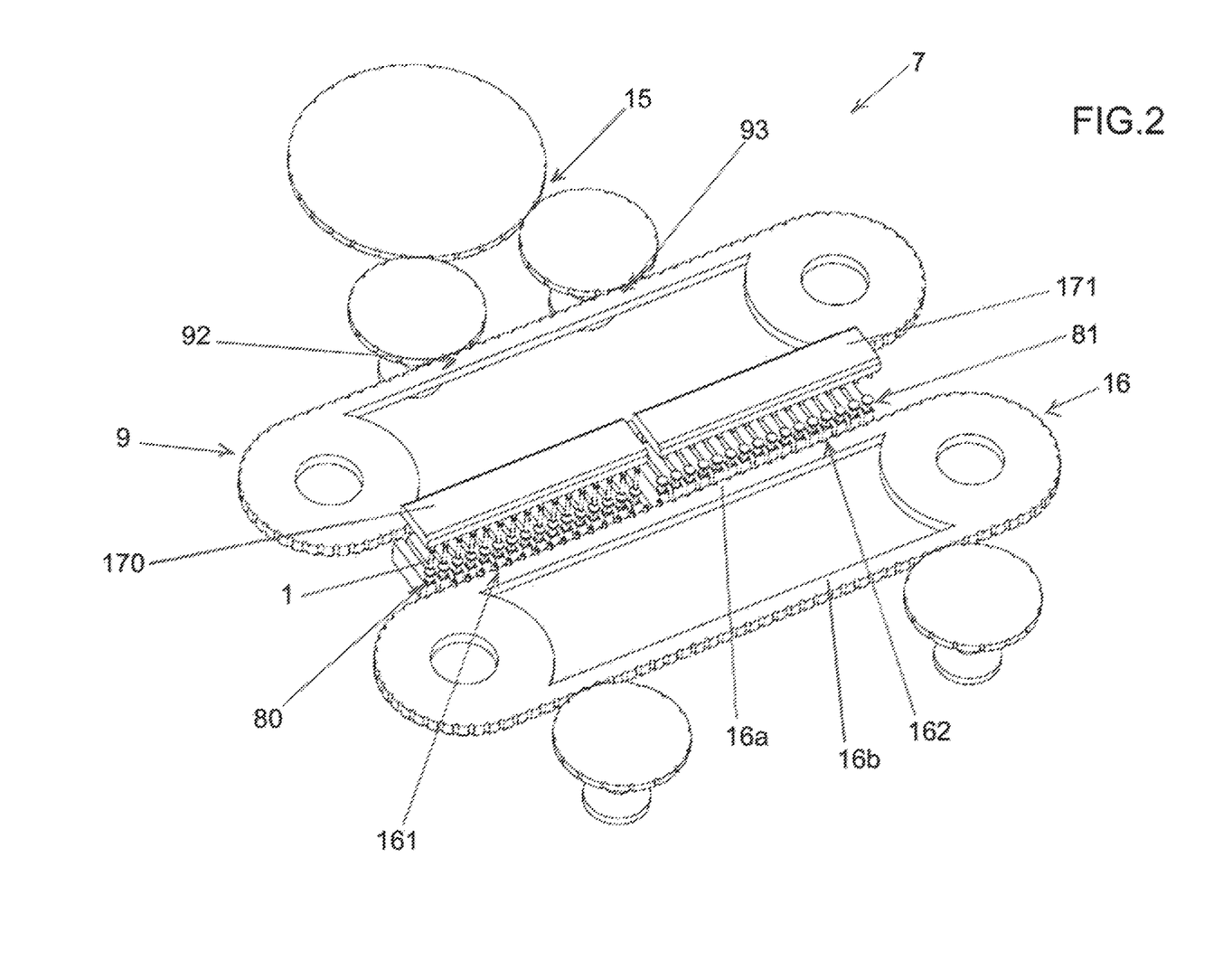
Figure 3:
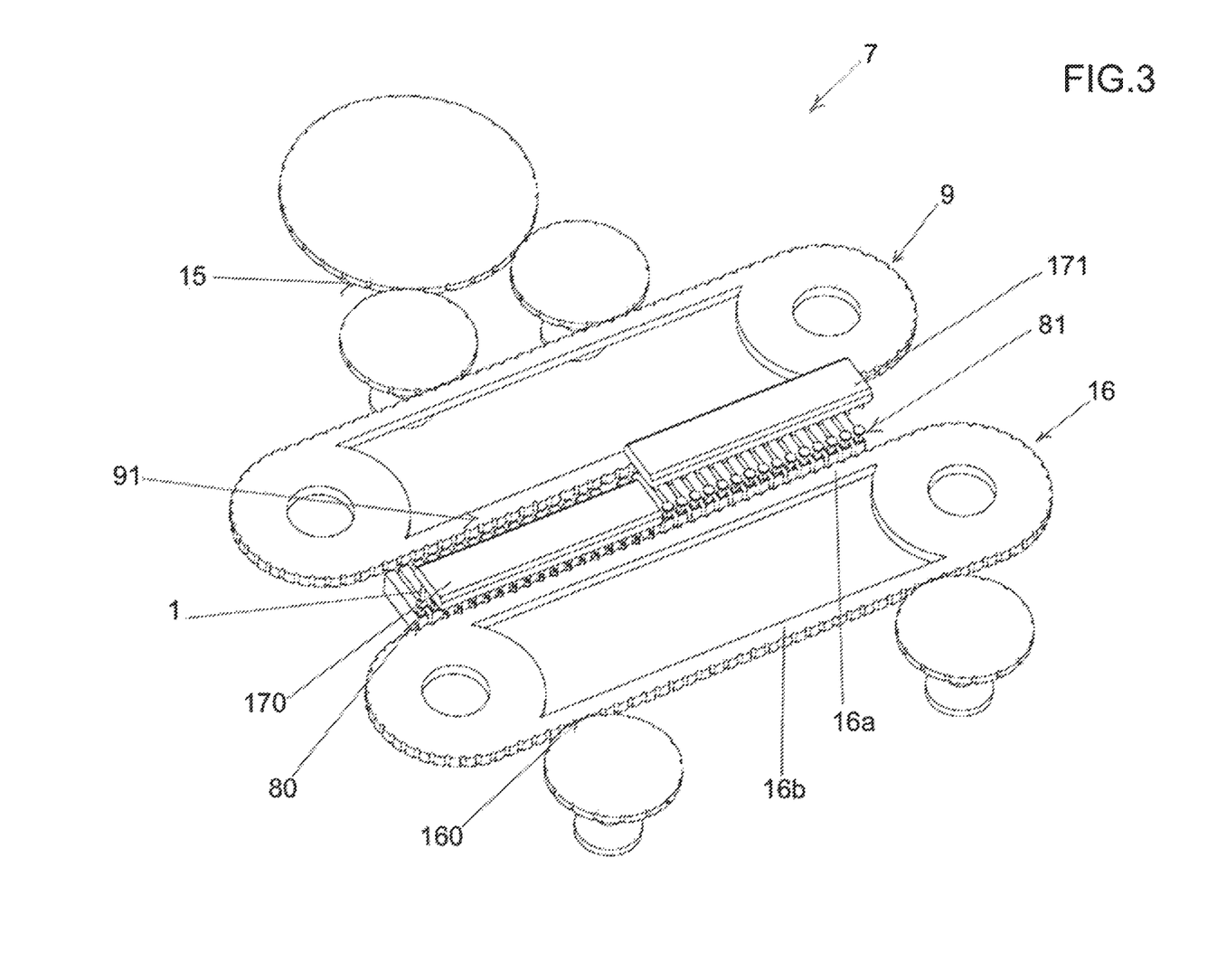
Figure 4:
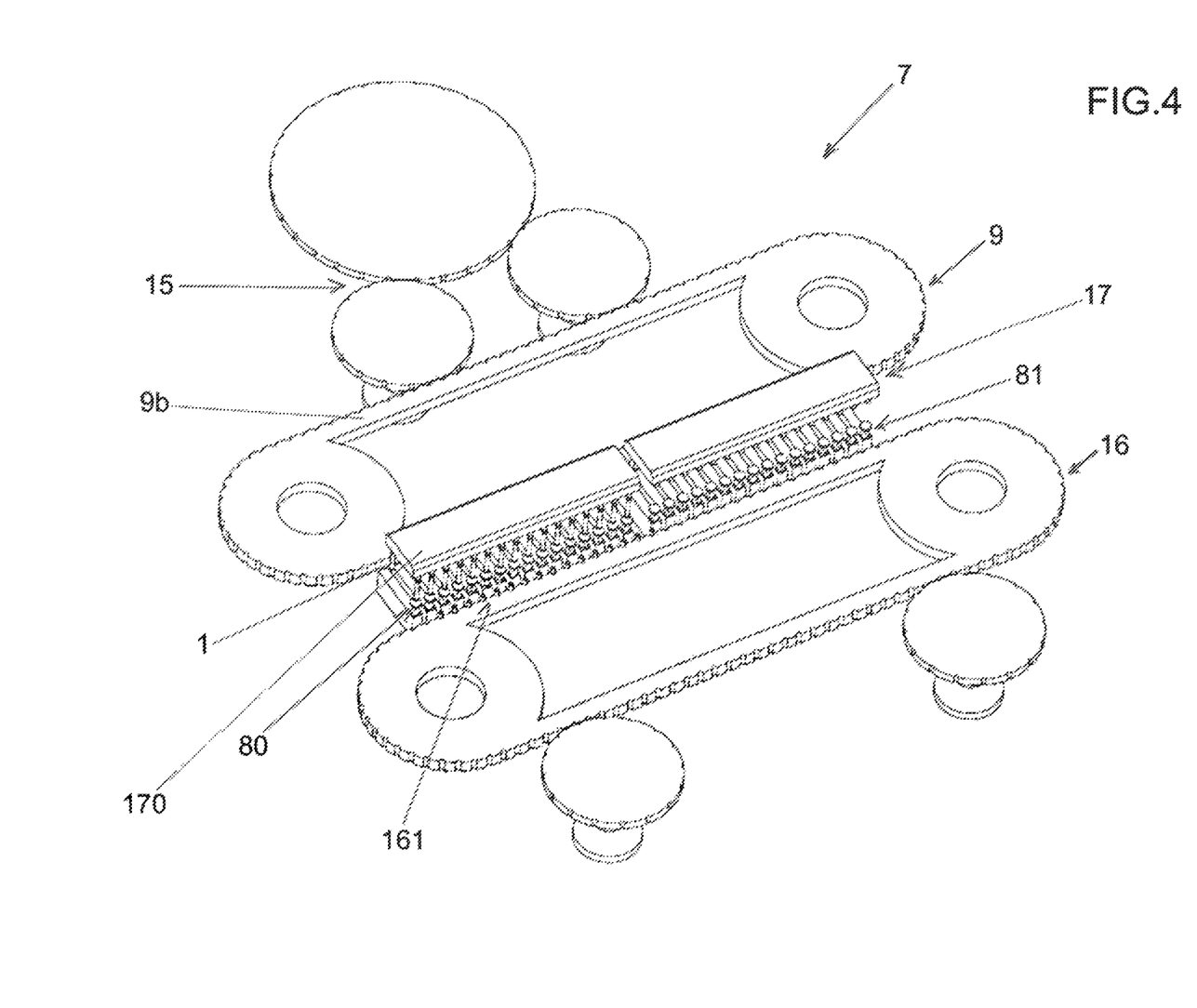
Figure 5:
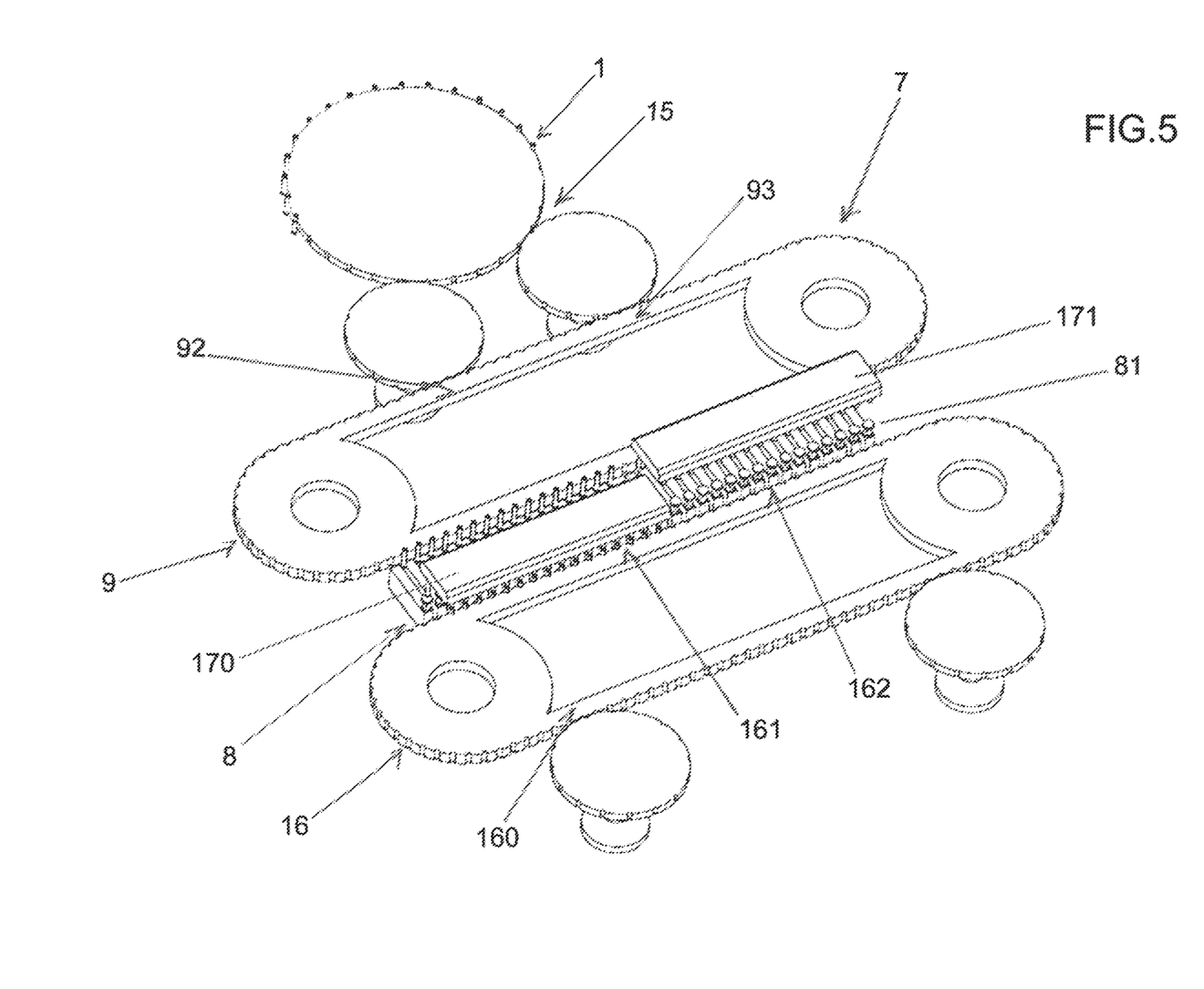
Figure 6:
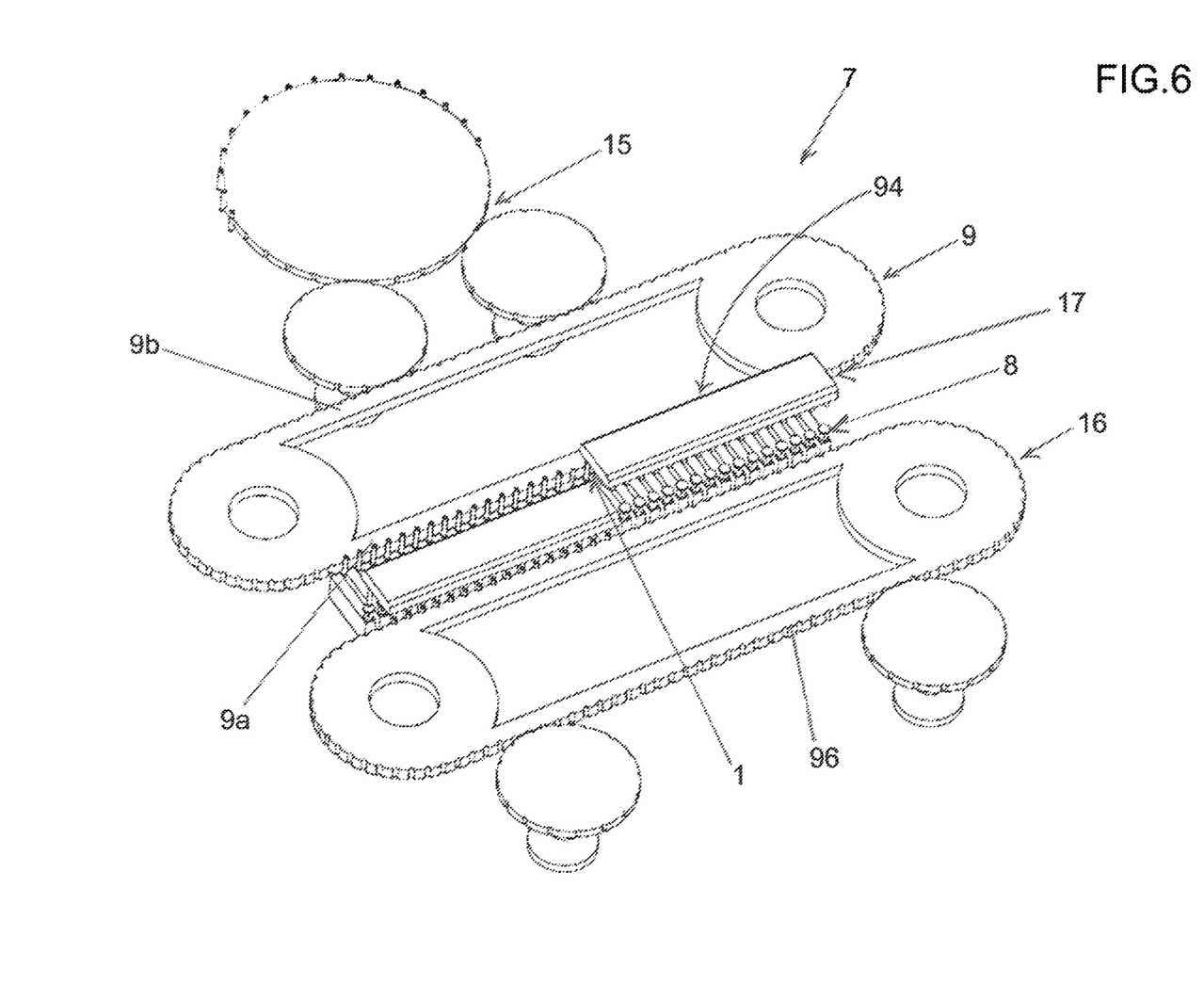
Figure 7:
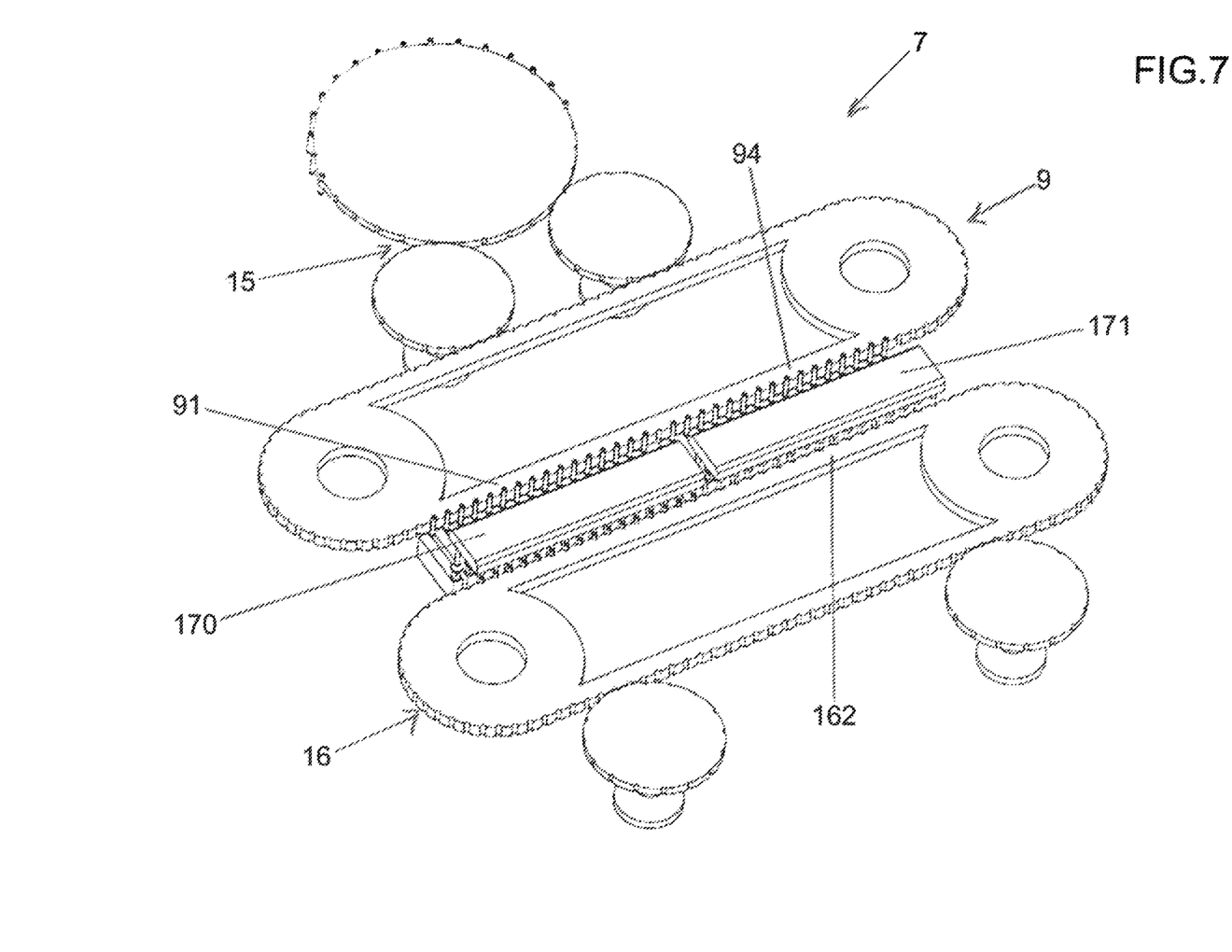
Figure 8:
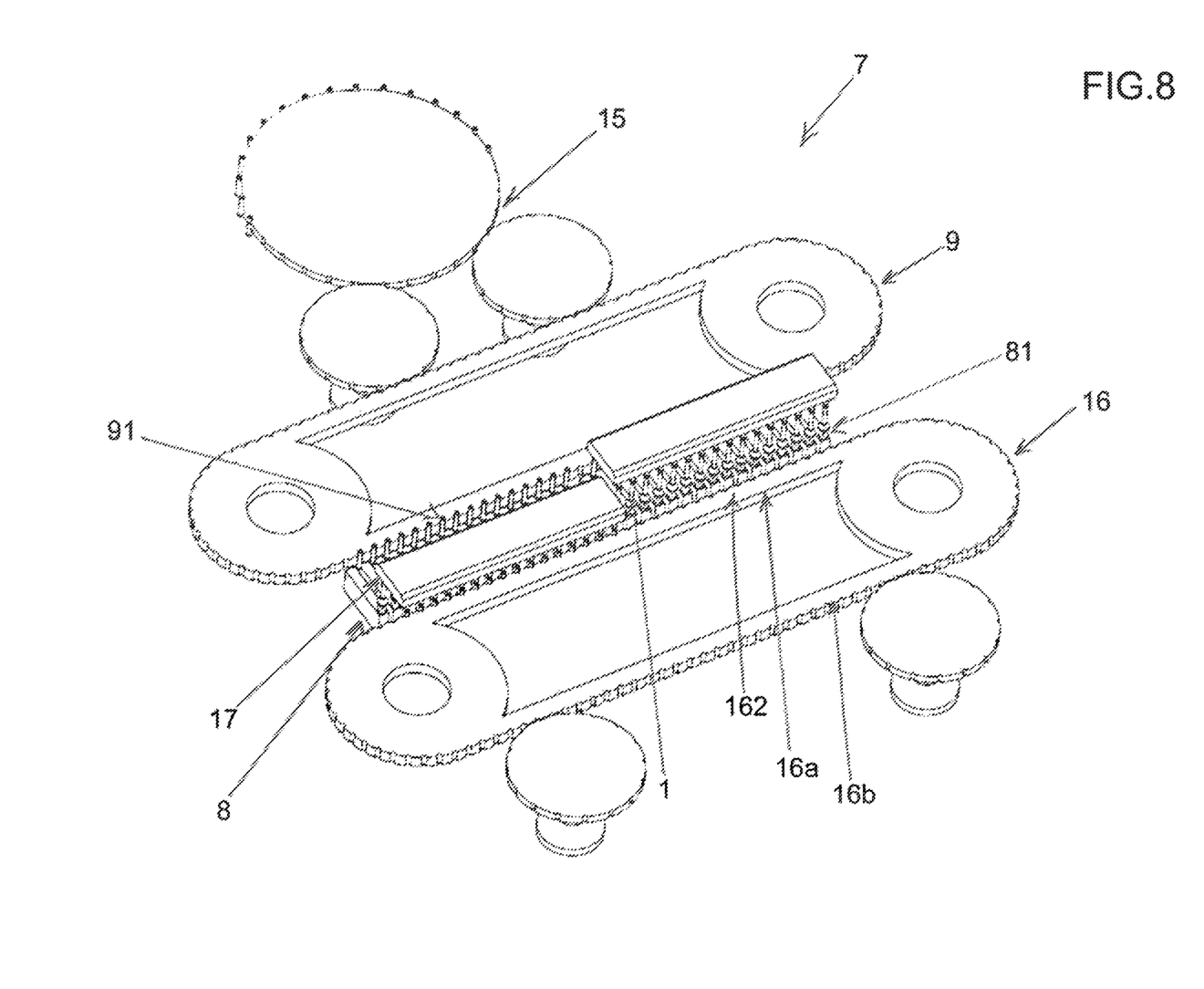

The device 7 comprises a first conveyor 9 which comprises: a first gripping portion 91 at which the container 10 without liquid 11 is received from the first weighing group 80 (FIGS. 3-4); a first release portion 92 at which the container 10 without liquid 11 is moved to a filling station 15 to fill the container 10 with the liquid 11 (FIG. 5); a second gripping portion 93 at which the container 10 containing liquid 11 is received from the filling station 15 (FIG. 6); a second release portion 94 at which the container 10 containing liquid 11 is moved to the second weighing group 81 (FIGS. 7-8).

Advantageously, the device 7 is extremely compact.

In particular, the first weighing group 80 comprises multiple load cells, each for weighing a container 10 without liquid 11. Similarly, the second weighing group 81 comprises multiple load cells, each for weighing a container 10 with liquid 11.

Advantageously, thanks to the simultaneous weighing of several containers 10 without liquid 11 and with liquid 11, the device 7 allows the control of all cartridges 1 (100% weighing) in reduced times.

Figure 9:
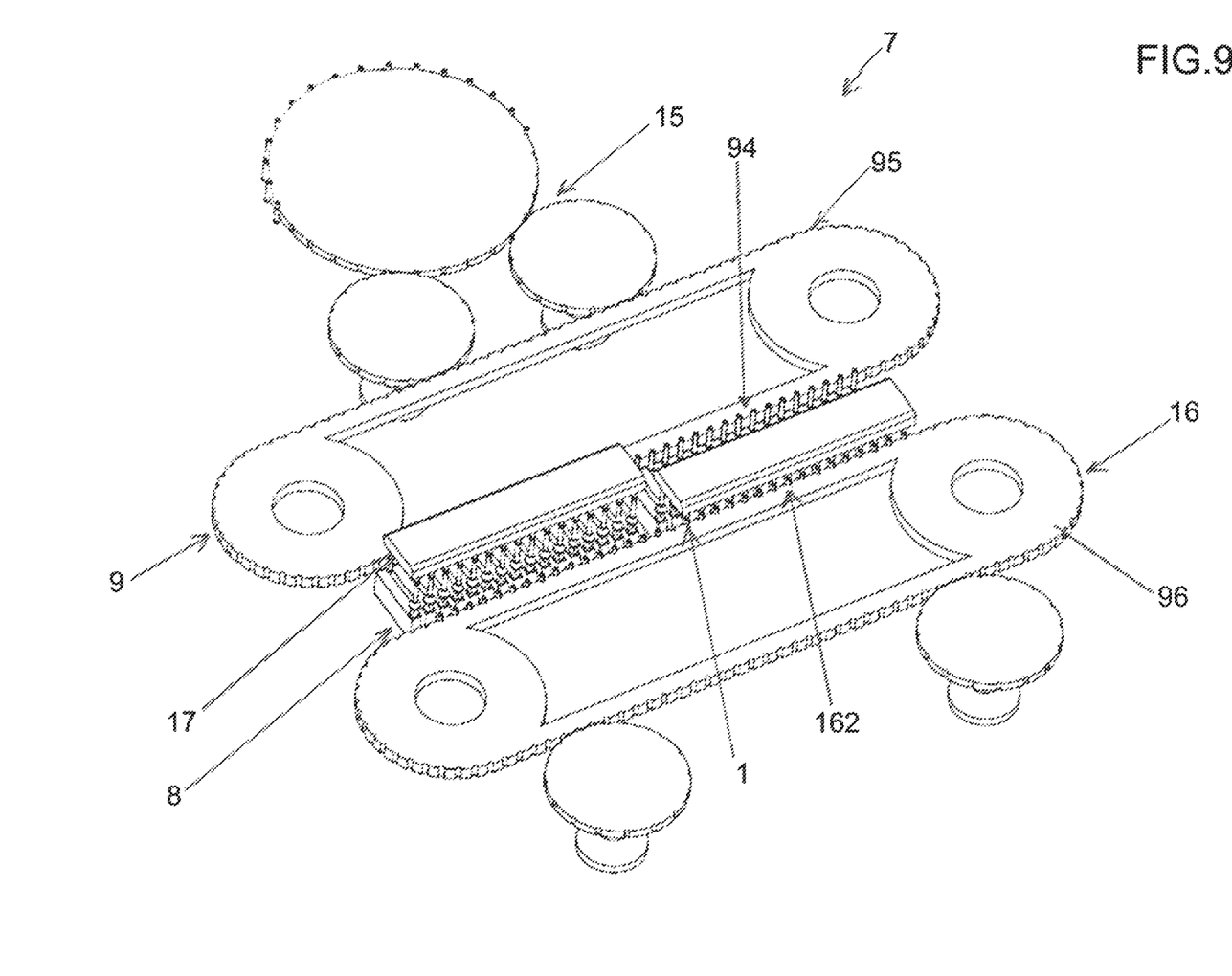

Preferably, the device 7 comprises a second conveyor 16 which comprises: a first gripping portion 160 at which the container 10 without liquid 11 is received (FIG. 1); a first release portion 161 at which the container 10 without liquid 11 is moved to the first weighing group 80 (FIG. 2); a second gripping portion 162 at which the container 10 with liquid 11 is received from the second weighing group 81 (FIG. 9).

The first conveyor 9 can be ring-shaped and can comprise a first branch 9a comprising the first gripping portion 91 and the second release portion 94 and a second branch 9b comprising the first release portion 92 and the second gripping portion 93.

Similarly, the second conveyor 16 can be ring-shaped and can comprise a first branch 16a comprising the first release portion 161 and the second gripping portion 162 and a second branch 16b comprising the first gripping portion 160.

Preferably, the first branch 9a of the first conveyor 9 and the first branch 16a of the second conveyor 16 are opposed. This allows to make the device 7 even more compact.

The measuring means 8 (i.e. the first weighing group 80 and the second weighing group 81) are arranged between the first branch 9a of the first conveyor 9 and the first branch 16a of the second conveyor 16.

Advantageously, the first weighing group 80 and the second weighing group 81 are side by side and compact.

Moreover, the device 7 can comprise gripping and releasing means 17 arranged at the measuring means 8 and comprising: a first element 170 for gripping the container 10 from the first release portion 161 of the second conveyor 16 and releasing it to the first weighing group 80 and for gripping the container from the first weighing unit 80 and releasing it to the first gripping portion 91 of the first conveyor 9; a second element 171 for gripping the container 10 from the second release portion 94 of the first conveyor 9 and releasing it to the second weighing group 81 and for gripping the container 10 from the second weighing group 81 and releasing it to the second gripping portion 162 of the second conveyor 16. The gripping and releasing means 17 are of the pick and place type. As mentioned above, the container 10 can have a longitudinal development along a respective development axis X.

The first conveyor 9 can comprise a pair of pulleys rotating about respective rotation axes parallel to one another and a chain 95 which forms a plurality of seats for receiving a container 10 of a cartridge 1 in each seat. Said seats are arranged to receive the containers 10 with the development axis X parallel to the rotation axes of the pulleys.

Likewise, also the second conveyor 16 can comprise a pair of pulleys rotating about respective rotation axes parallel to one another and a chain 96 which forms a plurality of seats for receiving a container 10 of a cartridge 1 in each seat. Said seats are arranged to receive the containers 10 with the development axis X parallel to the rotation axes of the pulleys.

The chain 95 of the first conveyor 9, in addition to rotating about the pulleys, is translated with a speed such that the first gripping station 91 and the second release station 94 are stationary with respect to the device 7. In other words, the pulleys of the first conveyor 9, in addition to rotating about the respective rotation axes, are translated linearly so as to allow the release and the withdrawal at the first gripping station 91 and at the second release station 94.

Similarly, the chain 96 of the second conveyor 16, in addition to rotating about the pulleys, is translated with a speed such that the first release station 161 and the second gripping station 162 are stationary with respect to the device 7. In other words, the pulleys of the second conveyor 16 in addition to rotating about the respective rotation axes, are translated linearly so as to allow the release and the withdrawal at the first release station 161 and at the second gripping station 162.

A further embodiment of the device 7 (not illustrated) is described in the following. In particular, said embodiment of the device 7 allows to determine the electrical capacity of the liquid 11 contained in the container 10.

The measuring means 8 comprise: a first conductor element 5 and a second conductor element 6 arranged opposite to each other in order to receive between them the liquid 11 contained in the cartridge 10; a charge supply for electrically charging the first conductor element 5 and the second conductor element 6; a measuring element for measuring the electrical capacity and/or the dissipation factor.

Advantageously, said device 7 is mechanically simple.

The container 10 of the cartridge 1 is made of a conductor material and the cartridge 1 comprises an absorbent element 12 arranged in the container 10 which holds the liquid 11 and which has a tubular shape defining a cavity 13. In this case, the first conductor element 5 is identified in the container 10 of the cartridge 1 and the second conductor element 6 is a tubular element which can be inserted into the cavity 13 of the absorbent element 12.

The device can comprise at least one seat shaped to receive a cartridge 1 and moving means for reciprocally moving the cartridge 1 and the second conductor element 6 from and towards an operating position in which the second conductor element 6 is at least partially inserted into the cavity 13 of the absorbent element 12.

With reference to FIG. 13, the first conductor element 5 is a plate, the second conductor element 6 is a plate and the device comprises means for conveying the cartridge between the first conductor element 5 and the second conductor element 6.

The invention claimed is:

1. A method for controlling the quantity of liquid (11) contained in a cartridge (1) for an aerosol generating device, wherein the cartridge (1) comprises a container (10) and a liquid (11) contained in the container (10); the method comprising:
    measuring the quantity of liquid (11) contained in the cartridge (1); and
    comparing the quantity of liquid (11) with a reference quantity of liquid;
wherein the step of measuring the quantity of liquid (11) comprises sequentially the following steps:
    weighing the container (10) of the cartridge (1) in a first weighing group (80);
    injecting a quantity of liquid (11) in the container (10) in a filling station (15);
    weighing the cartridge (1) in a second weighing group (81); and
    calculating the weight of the liquid (11) contained in the container (10);
    wherein a first conveyor (9) is provided comprising: a first gripping portion (91) at which it receives the container (10) without liquid (11) from the first weighing group (80); a first release portion (92) at which the container (10) without liquid (11) is moved to the filling station (15) to fill the container (10) with the liquid (11); a second gripping portion (93) at which it receives the container (10) containing liquid (11) from the filling station (15); and a second release portion (94) at which the container (10) containing liquid (11) is moved to the second weighing group (81);
    the method (7) is characterized in that it comprises a second conveyor (16) which comprises: a first gripping portion (160) at which the container (10) without liquid (11) is received; a first release portion (161) at which the container (10) without liquid (11) is moved to the first weighing group (80); and a second gripping portion (162) at which the container (10) containing liquid (11) is received from the second weighing group (81).

2. A device (7) for controlling the quantity of liquid (11) contained in a cartridge (1) for an aerosol generating device, wherein the cartridge (1) comprises a container (10) and a liquid (11) contained in the container (10) and wherein the device (7) comprises:
    measuring means (8) for measuring the quantity of liquid (11) contained in the cartridge (1) and comprising a first weighing group (80) for weighing at least one container (10) of a cartridge (1) before filling the same with the liquid (11) and a second weighing group (81) for weighing the container (10) containing liquid (11);
    a processing unit connected to the measuring means (8) for receiving the data measured by the measuring means (8) and comparing them with a reference quantity of liquid; and
    a first conveyor (9) which comprises: a first gripping portion (91) at which the container (10) without liquid (11) is received from the first weighing group (80); a first release portion (92) at which the container (10) without liquid (11) is moved to a filling station (15) for filling the container (10) with the liquid (11); a second gripping portion (93) at which the container (10) containing liquid (11) is received from the filling station (15); and a second release portion (94) at which the container (10) containing liquid (11) is moved to the second weighing group (81);

the device (7) is characterized by comprising a second conveyor (16) which comprises: a first gripping portion (160) at which the container (10) without liquid (11) is received; a first release portion (161) at which the container (10) without liquid (11) is moved to the first weighing group (80); and a second gripping portion (162) at which the container (10) containing liquid (11) is received from the second weighing group (81).

3. The device (7) according to claim 2, wherein:

the first conveyor (9) is ring-shaped and comprises a first branch (9*a*) comprising the first gripping portion (91) and the second release portion (94) and a second branch (9*b*) comprising the first release portion (92) and the second gripping portion (93);

the second conveyor (16) is ring-shaped and comprises a first branch (16*a*) comprising the first release portion (161) and the second gripping portion (162) and a second branch (16*b*) comprising the first gripping portion (160); and the first branch (9*a*) of the first conveyor (9) and the first branch (16*a*) of the second conveyor (16) are opposed.

4. The device (7) according to claim 3, wherein the measuring means (8) are arranged between the first branch (9*a*) of the first conveyor (9) and the first branch (16*a*) of the second conveyor (16).

5. The device (7) according to claim 2 and comprising gripping and releasing means (17) arranged at the measuring means (8) and comprising:

a first element (170) for gripping the container (10) from the first release portion (161) of the second conveyor (16) and releasing it to the first weighing group (80) and for gripping the container (10) from the first weighing group (80) and releasing it to the first gripping portion (91) of the first conveyor (9); and a second element (171) for gripping the container (10) from the second release portion (94) of the first conveyor (9) and releasing it to the second weighing group (81) and for gripping the container (10) from the second weighing group (81) and releasing it to the second gripping portion (162) of the second conveyor (16).

6. The device (7) according to claim 2, wherein:

the container (10) has a longitudinal development along a relative development axis (X);

the first conveyor (9) comprises a couple of pulleys rotating about respective rotation axes parallel to one another and a chain (95) which forms a plurality of seats for receiving a container (10) of a cartridge (1) in each seat; and said seats being arranged to receive the containers (10) with the development axis (X) parallel to the rotation axes of the pulleys.

\* \* \* \* \*